United States Patent
Gotfried

(10) Patent No.: US 9,814,578 B1
(45) Date of Patent: Nov. 14, 2017

(54) ORTHOPEDIC IMPLANTS

(71) Applicant: Yechiel Gotfried, Kiryat Motzkin (IL)

(72) Inventor: Yechiel Gotfried, Kiryat Motzkin (IL)

( * ) Notice: Subject to any disclaimer, the term of this patent is extended or adjusted under 35 U.S.C. 154(b) by 0 days.

(21) Appl. No.: 15/189,641

(22) Filed: Jun. 22, 2016

(51) Int. Cl.
*A61F 2/44* (2006.01)
*A61F 2/28* (2006.01)
*A61F 2/30* (2006.01)
*A61F 2/38* (2006.01)
*A61F 2/42* (2006.01)

(52) U.S. Cl.
CPC ........ *A61F 2/2846* (2013.01); *A61F 2/30767* (2013.01); *A61F 2/389* (2013.01); *A61F 2/4225* (2013.01); *A61F 2/4455* (2013.01); *A61F 2002/3092* (2013.01)

(58) Field of Classification Search
CPC ......... A61B 17/8095; A61F 2002/2825; A61F 2002/2892; A61F 2002/30158; A61F 2002/30266; A61F 2002/30281; A61F 2/28; A61F 2/4455; A61F 2/442; A61F 2/447; A61F 2/3094; A61F 2310/00011; A61F 2310/00359; A61F 2310/00017; A61F 2310/00023; A61F 2310/00029; A61F 2310/00179; A61F 2310/00329
USPC .......... 623/17.11–17.16, 18.11, 23.53, 23.58
See application file for complete search history.

(56) References Cited

U.S. PATENT DOCUMENTS 6,039,762 A * 3/2000 McKay ............... A61F 2/44
    606/247
6,902,578 B1 6/2005 Anderson et al.
2004/0006390 A1 * 1/2004 Duarte ............... A61F 2/447
    623/17.11
2004/0193270 A1 * 9/2004 DiMauro ........... A61L 27/3834
    623/17.11
2005/0010223 A1 1/2005 Gotfried
2005/0010292 A1 1/2005 Carrasco
2005/0246021 A1 11/2005 Ringeisen et al.
2005/0261767 A1 * 11/2005 Anderson ............ A61F 2/28
    623/16.11

(Continued)

FOREIGN PATENT DOCUMENTS

FR     2919488 A1   2/2009
WO   2007064950 A2   6/2007
WO   2013179142 A1  12/2013

OTHER PUBLICATIONS

Related U.S. Appl. No. 14/836,664, filed Aug. 26, 2015, First Named Inventor: Yechiel Gotfried, Title: "Orthopedic Implants".

(Continued)

*Primary Examiner* — Pedro Philogene
(74) *Attorney, Agent, or Firm* — Holtz, Holtz & Volek PC

(57) ABSTRACT

Apparatus is provided for placement at an anatomical site, including an orthopedic implant, which has front and rear ends, a top and bottom, right and left sides, and a central part connecting the sides. A distance between the top and the bottom is (a) greater at a first location at one of the sides than at a second location opposite the first location at the other side, and (b) greater at a third location at the front end than at a fourth location opposite the third location at the rear end. At least a portion of the implant is a porous matrix, which is shaped to define pores that extend through the porous matrix in at least each of: (a) a front-to-rear direction, (b) a left-to-right direction, and (c) a top-to-bottom direction.

17 Claims, 11 Drawing Sheets

(56) References Cited

U.S. PATENT DOCUMENTS

| | | | |
|---|---|---|---|
| 2007/0016295 A1* | 1/2007 | Boyd | A61F 2/28 623/17.11 |
| 2007/0050029 A1* | 3/2007 | Carrasco | A61F 2/4455 623/17.11 |
| 2008/0195099 A1 | 8/2008 | Minas | |
| 2009/0177203 A1 | 7/2009 | Reiley | |
| 2010/0152853 A1* | 6/2010 | Kirschman | A61F 2/447 623/17.11 |
| 2010/0305712 A1 | 12/2010 | Ringeisen et al. | |
| 2011/0004311 A1* | 1/2011 | Semler | A61F 2/3872 623/17.16 |
| 2013/0116793 A1* | 5/2013 | Kloss | A61F 2/442 623/17.16 |
| 2013/0184826 A1* | 7/2013 | Thaiyananthan | A61F 2/442 623/17.16 |
| 2016/0128748 A1 | 5/2016 | Tepic et al. | |

OTHER PUBLICATIONS

Office Action (Non-Final Rejection) dated Aug. 28, 2017 issued in U.S. Appl. No. 15/435,599.

\* cited by examiner

ORTHOPEDIC IMPLANTS

CROSS-REFERENCE TO RELATED APPLICATIONS

The present application is related to International Application No. PCT/IL2015/051261 to Gotfried, filed Dec. 28, 2015, which claims the priority of U.S. application Ser. No. 14/836,664 to Gotfried, filed Aug. 26, 2015, and Provisional U.S. Application Ser. No. 62/097,322, filed Dec. 29, 2014. Each of these applications is incorporated herein by reference.

FIELD OF THE INVENTION

Applications of the present invention relate in general to orthopedic implants, and specifically, to orthopedic implants for changing an angular orientation of a bone.

BACKGROUND

In some pathologies, the patella is too close to the trochlea of the femur, and/or is improperly aligned with respect to the trochlea. In other pathologies, an intervertebral space in the spinal column is too small, and/or normal lordosis of the spinal column is absent. Multiple other pathologies relate to inappropriately aligned bones.

SUMMARY OF THE INVENTION

Applications of the present invention include methods for operating on a subject, in order to treat pathological conditions. For example, an orthopedic implant having a porous matrix may be inserted into an osteotomy in a tibia of the subject, bone graft material being coupled to the implant. By implanting the implant in the osteotomy, the patella of the subject is rotated about the axis of insertion, and a distance of the patella from the anterior distal portion of the femur (i.e., the trochlea of the femur) is increased. The orthopedic implant includes a front end, a rear end, a top, a bottom, a right side, and a left side. To facilitate the rotation of the patella, the distance between the top and the bottom is greater at one of the sides than at the other one of the sides. In addition to the porous matrix, the implant is typically shaped to define one or more passageways passing through the implant, the passageways facilitating the coupling of bone graft material to the implant.

There is therefore provided, in accordance with a first application of the present invention, apparatus for placement at an anatomical site, the apparatus including: an orthopedic implant, including:
  a front end,
  a rear end,
  a top,
  a bottom,
  a right side,
  a left side, and
  a central part connecting the right and left sides,
  a distance between the top and the bottom being (a) greater at a first location at one of the sides than at a second location opposite the first location at the other one of the sides, and (b) greater at a third location at the front end than at a fourth location opposite the third location at the rear end,
  at least a portion of the implant being shaped to define a porous matrix, the porous matrix being shaped to define pores that extend through the porous matrix in at least each of: (a) a front-to-rear direction, (b) a left-to-right direction, and (c) a top-to-bottom direction.

For some applications, at least one of the sides of the implant is shaped to define at least one passageway that passes through the side, the passageway having a diameter larger than an average diameter of the pores.

For some applications, the implant defines at least one passageway that passes through the implant from the top of the implant to the bottom of the implant, the passageway having a diameter larger than an average diameter of the pores.

For some applications, the central part of the implant defines the porous matrix.

For some applications, the central part is shaped to define at least one passageway that passes through the implant, the passageway having a diameter larger than an average diameter of the pores.

For some applications, the implant is shaped to define an H-shape, when viewed in a direction from the top to the bottom.

For some applications, at least 90 percent of a volume of the implant that includes the pores includes the porous matrix.

For some applications, at least a portion of the front end, the rear end, the top, the bottom, the right side, or the left side of the implant defines a portion of the porous matrix.

For some applications, the implant is for use with a tool and the implant further includes a connection interface that facilitates a connection of the implant to the tool.

For some applications, the connection interface is front-facing.

For some applications, the connection interface is shaped to define a threaded hole.

For some applications, the tool includes a rod that is fixed to the implant at the connection interface.

For some applications, a connection between the rod and the implant is configured to be breakable at the connection interface due to a size of the connection interface.

For some applications, the distance between the top and the bottom is at least 0.5 mm greater at the first location at one of the sides than at the second location opposite the first location at the other one of the sides, and the distance between the top and the bottom is at least 0.5 mm greater at the third location at the front end than at the fourth location opposite the third location at the rear end.

For some applications, the distance between the top and the bottom is greater at the front end than at respective, corresponding opposite locations on the rear end, on both of the left and the right sides of the implant.

For some applications, the distance between the top and the bottom is at least 0.5 mm greater at the front end than at the respective, corresponding opposite locations on the rear end, on both of the left and the right sides of the implant.

For some applications, the apparatus further includes a bone graft material.

For some applications, the implant consists of a metal.
For some applications, the implant consists of a plastic.
For some applications, the implant consists of bone graft material.

There is further provided, in accordance with a second application of the present invention, apparatus for placement at an anatomical site, the apparatus including:
  an orthopedic implant, including:
  a front end,
  a rear end,
  a top,
  a bottom, a right side,
a left side, and
a connection interface that facilitates a connection of the implant to the tool,
a distance between the top and the bottom being (a) greater at a first location at one of the sides at the front end than at a second location opposite the first location at the front end of the other one of the sides, and (b) greater at a third location at the front end than at a fourth location opposite the third location at the rear end, and
at least a portion of the implant being shaped to define a porous matrix, the porous matrix being shaped to define pores that extend through the porous matrix in at least each of: (a) a front-to-rear direction, (b) a left-to-right direction, and (c) a top-to-bottom direction.

It is noted that any of the various applications described hereinabove in the context of the first application of the present invention may be applied with the second application of the present invention as well.

There is further provided, in accordance with an application of the present invention, a method for operating on a subject, the method including:
providing an orthopedic implant for bone realignment; and
by inserting, along an axis of insertion, the orthopedic implant into an anatomical site, changing an angular orientation of a first portion of bone with respect to a second portion of bone by rotating the first portion of bone about (a) the axis of insertion, and (b) an axis that is perpendicular to the axis of insertion,
the method being performed using the orthopedic implant, the orthopedic implant including:
a front end,
a rear end,
a top,
a bottom,
a right side,
a left side, and
a central part connecting the left and right sides,
a distance between the top and the bottom being (a) greater at a first location at one of the sides than at a second location opposite the first location at the other one of the sides, and (b) greater at a third location at the front end than at a fourth location opposite the third location at the rear end,
at least a portion of the implant being shaped to define a porous matrix, the porous matrix being shaped to define pores that extend through the porous matrix in at least each of: (a) a front-to-rear direction, (b) a left-to-right direction, and (c) a top-to-bottom direction.

For some applications, inserting the orthopedic implant into the anatomical site includes inserting the orthopedic implant into an anatomical site that is surrounded at least in part by one or more bones.

For some applications, the method includes creating an osteotomy at the anatomical site prior to inserting the orthopedic implant into the anatomical site.

For some applications, the anatomical site is a space between a first vertebra and a second vertebra of the subject,
the first portion of bone is the first vertebra,
the second portion of bone is the second vertebra, and
the method further includes increasing a distance between the first and second vertebra, and changing a biplanar angular orientation of the first vertebra with respect to the second vertebra, by inserting the implant.

For some applications:
the anatomical site is an osteotomy within a metatarsal bone of the subject, the first portion of bone is a first portion of the metatarsal bone,
the second portion of bone is a second portion of the metatarsal bone, and
the method includes changing a biplanar angular orientation of the first portion of the metatarsal bone with respect to the second portion of the metatarsal bone by inserting the implant.

For some applications:
the anatomical site is an osteotomy within a tibia of the subject,
the first portion of bone is a first portion of the tibia,
the second portion of bone is a second portion of the tibia that is more distal than the first portion of the tibia, and
the method further includes changing a biplanar angular orientation of the first portion of the tibia with respect to the second portion of the tibia by inserting the implant.

There is further provided, in accordance with an application of the present invention, a method for operating on a subject, the method including:
creating an osteotomy in a tibia of the subject; and
by inserting, along an axis of insertion, a biaxial realignment orthopedic implant into the osteotomy:
changing an angular orientation of a patella of the subject with respect to a trochlea of a femur of the subject by rotating the patella about the axis of insertion, by:
changing an angular orientation of the tuberosity of the tibia of the subject with respect to another portion of the tibia by rotating the tuberosity of the tibia about the axis of insertion, and
increasing a distance of the patella from the trochlea by pivoting the tuberosity of the tibia with respect to a point of contact between the tuberosity of the tibia and another portion of the tibia,
the method being performed using the orthopedic implant, the orthopedic implant including:
a front end,
a rear end,
a top,
a bottom,
a right side,
a left side, and
a central part connecting the right and left sides,
a distance between the top and the bottom being (a) greater at a first location at one of the sides than at a second location opposite the first location at the other one of the sides, and (b) greater at a third location at the front end than at a fourth location opposite the third location at the rear end,
at least a portion of the implant being shaped to define a porous matrix, the porous matrix being shaped to define pores that extend through the porous matrix in at least each of: (a) a front-to-rear direction, (b) a left-to-right direction, and (c) a top-to-bottom direction.

The present invention will be more fully understood from the following detailed description of applications thereof, taken together with the drawings, in which:

DETAILED DESCRIPTION OF THE DRAWINGS

Reference is made to FIGS. 1A-10, which are schematic illustrations of an orthopedic implant 20 for implanting in an anatomical site, in accordance with some applications of the present invention. Typically, the anatomical site is surrounded at least in part by one or more bones. For example, implant 20 may be implanted in a bone (e.g., an osteotomy, such as an osteotomy in a tibia), or a space between bones.

Figure 8:
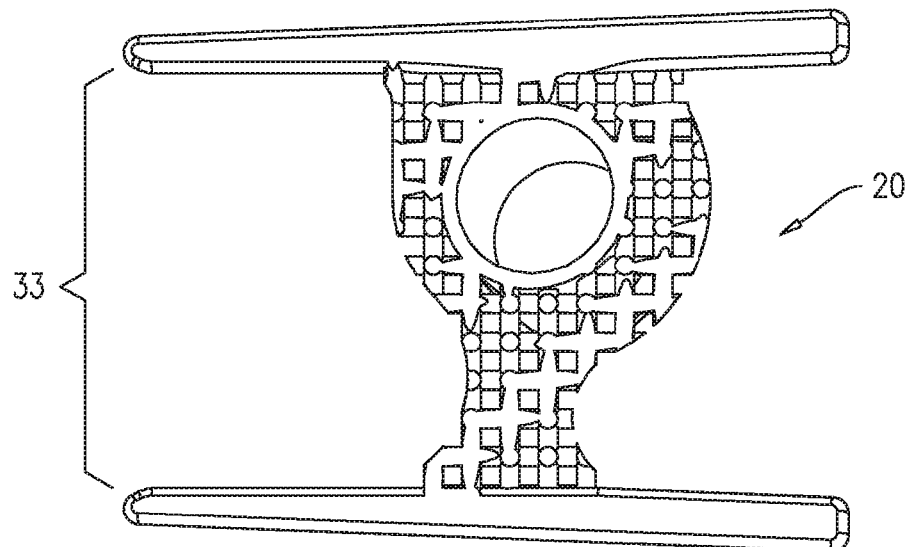

Implant 20 comprises a front end 22, a rear end 24, a top 26, a bottom 28, a right side 30, and a left side 32. Implant 20 typically additionally comprises a central part 33 connecting right and left sides 30 and 32 (as shown in FIGS. 1-9, but not shown in FIG. 10). Thus, implant 20 of FIGS. 1-9 is shaped to define an H-shape, when viewed in a direction from the top surface to the bottom surface (FIG. 8).

As further described hereinbelow, e.g., with reference to FIG. 13, one function of implant 20 is to change an angular orientation of one bone portion (i.e., part or all of a bone) with respect to another bone portion. To facilitate this function, a distance D0 between top 26 and bottom 28 at one of the sides is greater than a distance D1 between the top and bottom at the other side, along at least a portion of the sides. (For convenience, the distance between the top and bottom of the implant may be referred to below as the "height" of the implant.) In particular, D0 at a first location 34 at one of the sides is greater than D1 at a second location 36 opposite the first location at the other one of the sides. In some applications, D0 is greater than D1 along at least 80% of one of the sides. In some applications, for at least one instance of the first location and second location, D0 is at least 0.5 mm greater, e.g., at least 2.5 mm greater, and/or less than 20 mm greater, than D1. In other words, at at least one pair of opposite locations, the height at one of the sides is at least 0.5 mm greater and/or less than 20 mm greater than the height of the other one of the sides. Alternatively or additionally, at at least one pair of opposite locations, D0 is at least 0.5% greater than D1.

Typically, implant 20 is also shaped such that a distance D3 between the top and bottom at the front end is greater (e.g., 0.5% greater) than a distance D2 between the top and bottom at the rear end, along at least a portion of the ends. In particular, D3 at a third location 38 at the front end is greater than D2 at a fourth location 40 opposite the third location at the rear end. In some applications, D3 is greater than D2 along at least 80% of one of the ends. In general, this shape facilitates changing a second angular orientation of a bone portion, and/or facilitates the wedging of the implant within an anatomical site. In some applications, a distance D7 between the sides at the front end is greater than the distance D4 between the sides at the rear end.

Typically, bone graft material is inserted into the anatomical site along with implant 20, the bone graft material helping to stimulate bone formation in the anatomical site. (It is noted that in the context of the claims and specification of the present application, "bone graft material" includes any type of bone graft or bone graft substitute.) For some applications, at least a portion of implant 20, e.g., some or all of central part 33, is shaped to define a porous matrix, the porous matrix being shaped to define pores that extend through the porous matrix in at least each of: (a) a front-to-rear direction, (b) a left-to-right direction, and (c) a top-to-bottom direction. The pores may thus extend in many "diagonal" directions, i.e., combinations of (a), (b), and (c), which are not solely (a), (b), or (c). While not wishing to be limited by any particular dimensions for the pores, the inventor notes that the pores may be, for some applications, tens or hundreds of microns in size (e.g., in diameter). For some purposes, e.g., depending on the type of bone graft to be used, larger or smaller pores are suitable.

Figure 10:
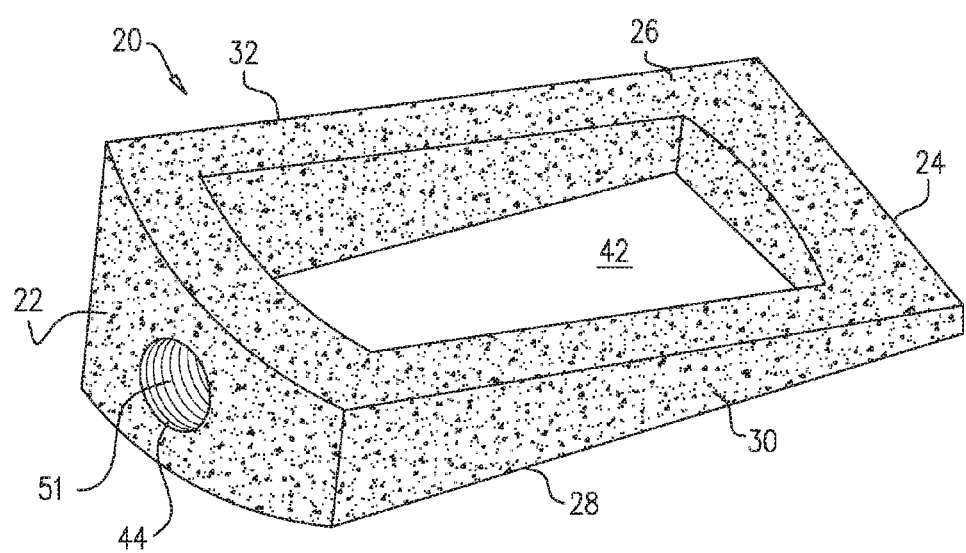
FIG. 10 is a schematic illustration of an orthopedic implant, in accordance with some applications of the present invention.

At least a portion of the front end, the rear end, the top, the bottom, the right side, or the left side of implant 20 typically defines a portion of the porous matrix. For example, FIGS. 1A and 5 respectively show a portion of the top and bottom of the implant defining a portion of the porous matrix. FIG. 10 additionally shows the front end, the rear end, the right side, and the left side defining a portion of the porous matrix.

Typically, but not necessarily, implant 20 is additionally shaped to define one or more passageways 42 passing through the implant, and the bone graft material is disposed within the pores of the porous matrix and/or within passageways 42. Typically, at least one of the passageways passes from the top to the bottom and/or through one or both of the sides of the implant. The passageways typically have a diameter larger than an average diameter of the pores, as shown for example in FIG. 1A.

Figure 1A:
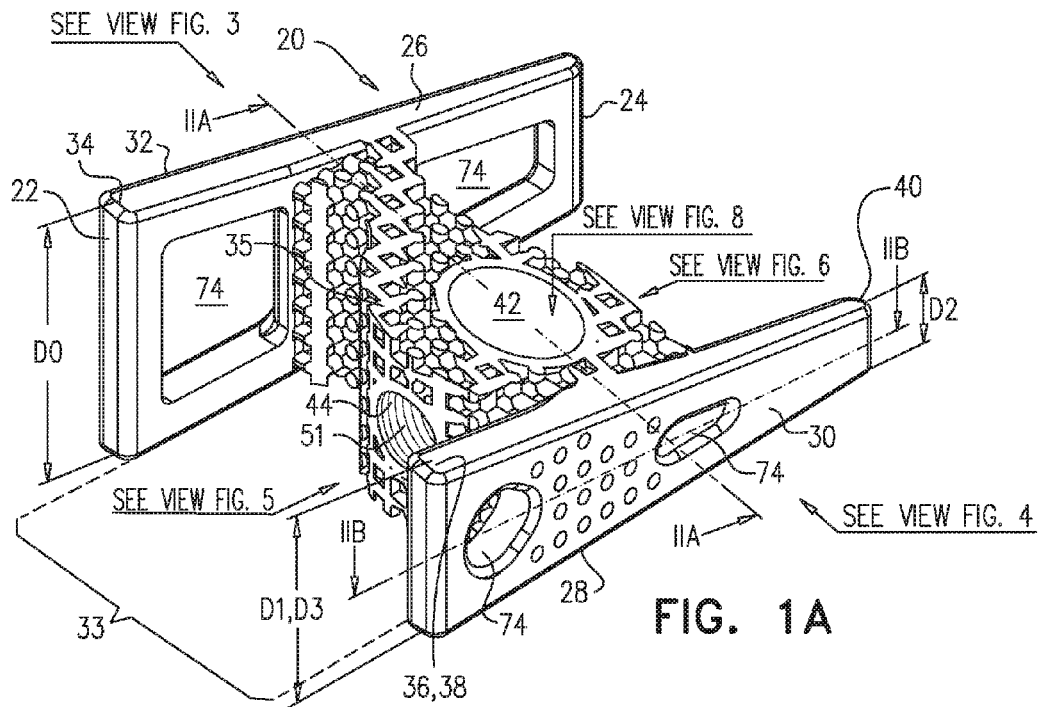
FIGS. 1A, 1B, 2A, 2B, 3, 4, 5, 6, 7 and 8 are schematic illustrations of an orthopedic implant for implanting in an anatomical site, FIGS. 2A and 2B showing a cross section of the implant, in accordance with some applications of the present invention.
Figure 1B:
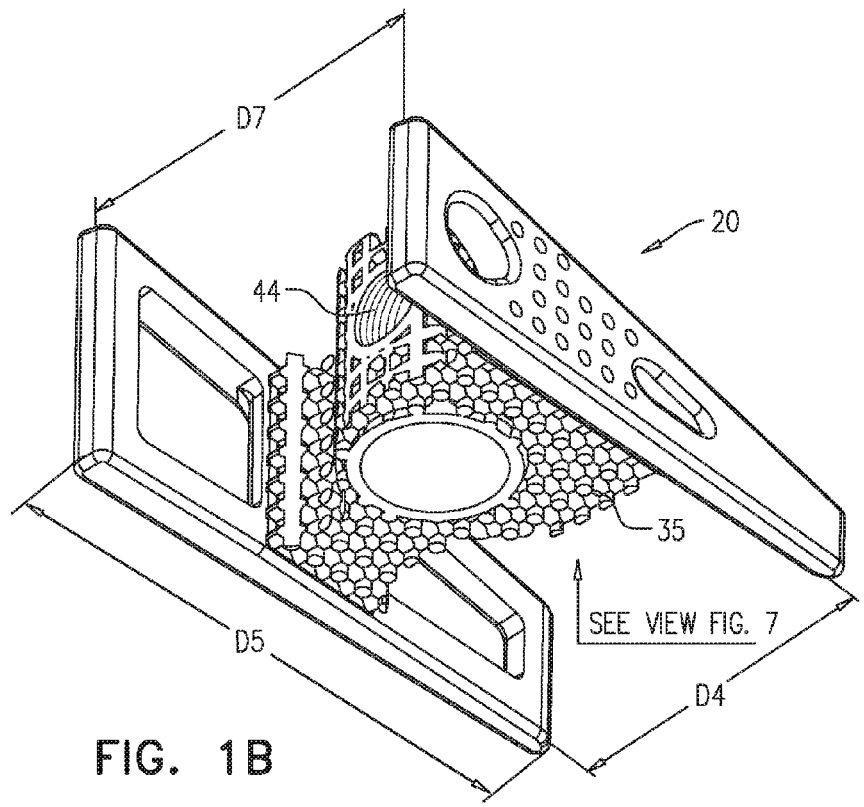
Figure 2A:
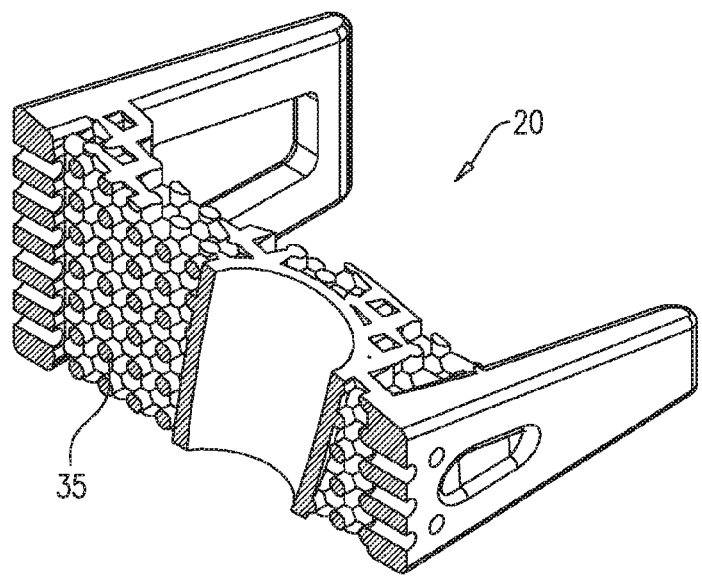
Figure 2B:
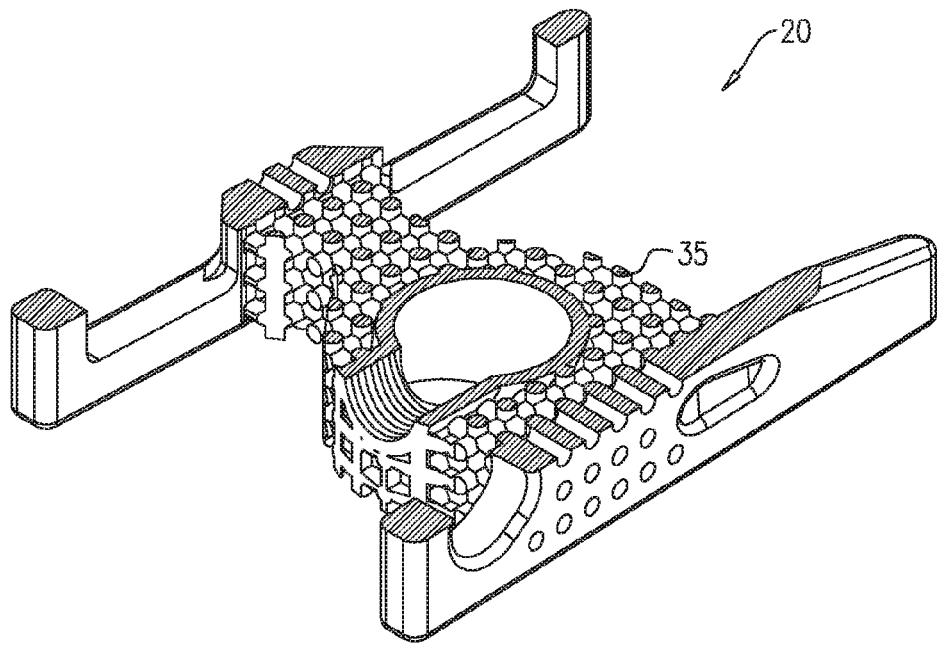
Figure 3:
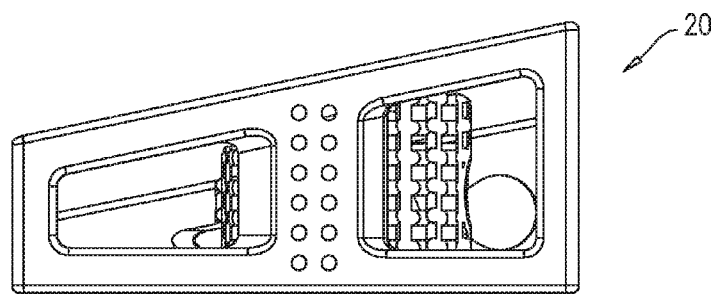
Figure 4:
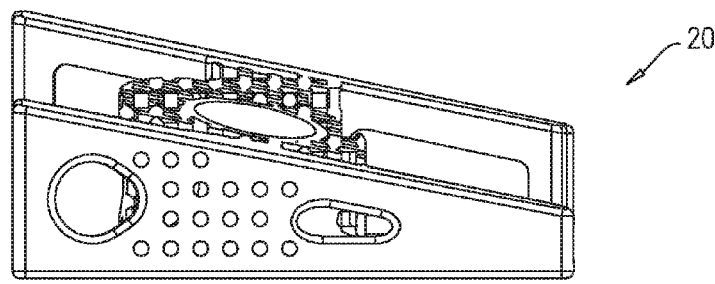
Figures 5, 6:
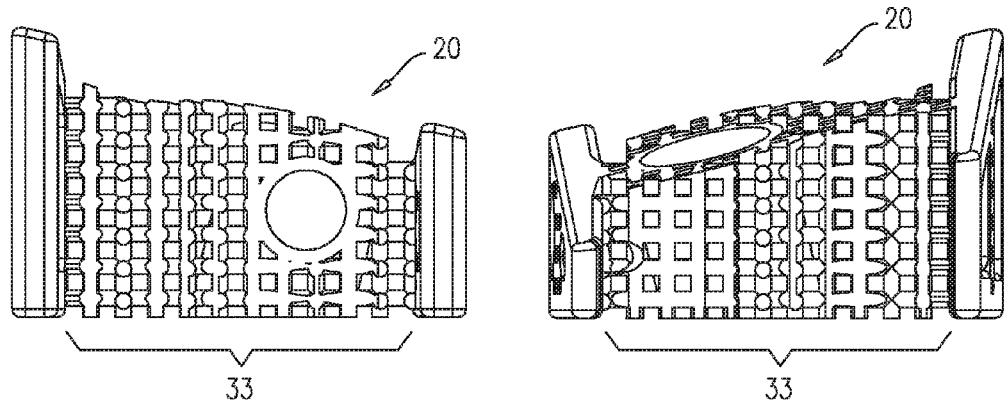
Figure 7:
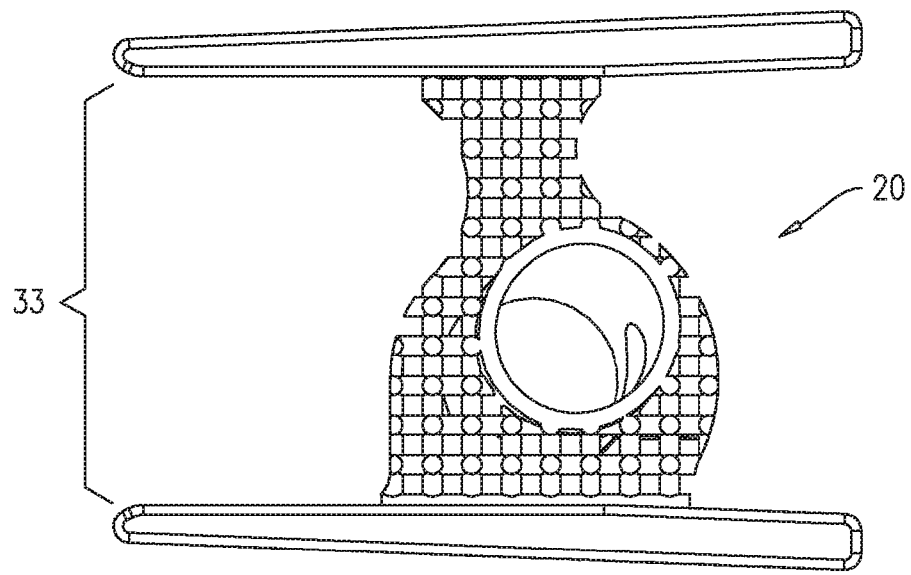

In some applications, at least 50%, for example, at least 80% (e.g., at least 90%) of the front end, rear end, top, bottom, right side, and/or left side is shaped to define openings to at least some of the passageways. FIG. 3 shows an example of this when implant 20 is viewed from the side. Similarly, FIG. 10 shows the implant having porous top, bottom, and side surfaces, and a large central passageway 42. Alternatively or additionally, at least 60 percent (e.g., 90 percent) of a volume of the implant that includes the pores comprises the porous matrix. The characteristics described in this paragraph typically allow for a relatively large amount of bone graft material to be inserted into the anatomical site. Alternatively or additionally, to facilitate insertion of bone graft material, the implant may be shaped to define a relatively large number of passageways, e.g., at least 5, 10, or more. Alternatively or additionally, the openings to the passageways may be relatively large, to facilitate insertion of bone graft material, and/or to facilitate access and/or coupling of a tool (e.g., an implantation tool) to the implant. For example, FIGS. 1A-9 shows large lateral openings 74.

In some applications, some of the openings may be used for passing a drill-alignment tool therethrough. For example, alignment techniques described in US 2005/0010223 to Gotfried, which is incorporated herein by reference, and shown in FIGS. 6 and 8 thereof, may be used for this purpose.

Figure 9:
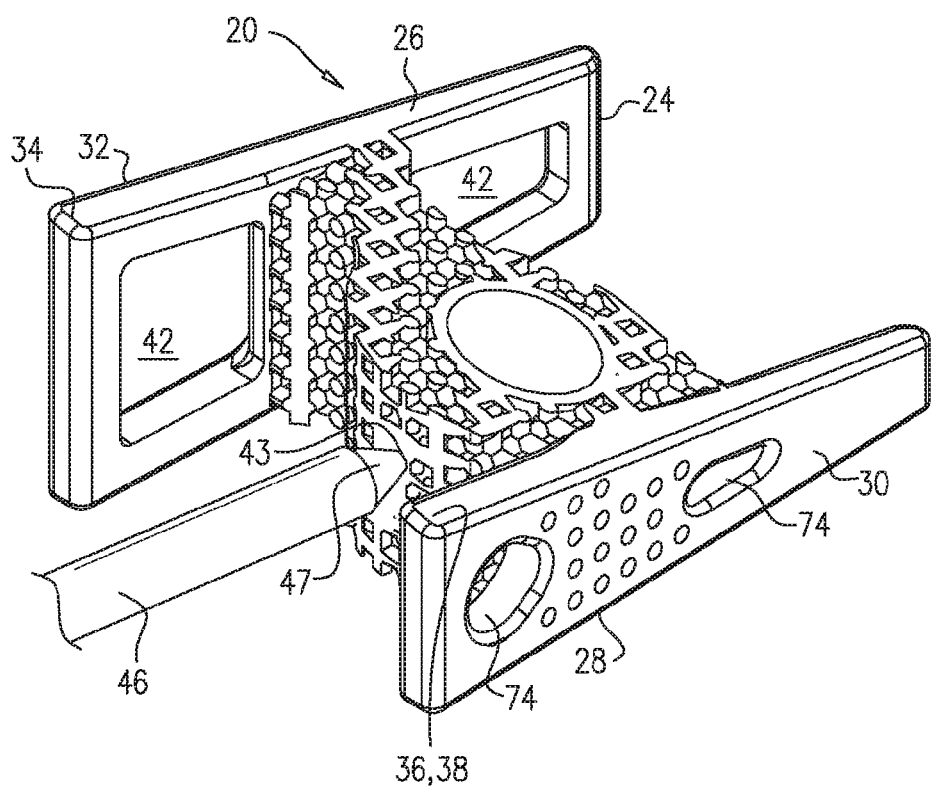
FIG. 9 is a schematic illustration of an orthopedic implant and a tool, in accordance with some applications of the present invention.

Typically, implant 20 comprises a connection interface 44, such as a threaded hole 51, which facilitates a connection of the implant to a tool, e.g., an implantation tool. (Although connection interface 44 is typically front-facing, it may also face in a different direction; for example, side-facing lateral openings 74 may be considered connection interfaces.) For some applications, e.g., as shown in FIG. 9, the tool comprises a rod 46 that is fixed to the implant at connection interface 44. A connection 43 between rod 46 and implant 20 is configured to be breakable at connection interface 44 due to a size of the connection interface. For example, a distal portion 47 of rod 46 may be narrowed, such that the physician holding the rod may be able to break the rod from the implant at connection 44 by applying up and down bending motion to the rod or by applying side to side bending motion to the rod.

In some applications, the implant consists entirely of a metal, e.g., a metallic alloy and/or titanium. In other applications, the implant consists entirely of a plastic (e.g., polyether ether ketone), or entirely of bone graft material.

Figure 11:
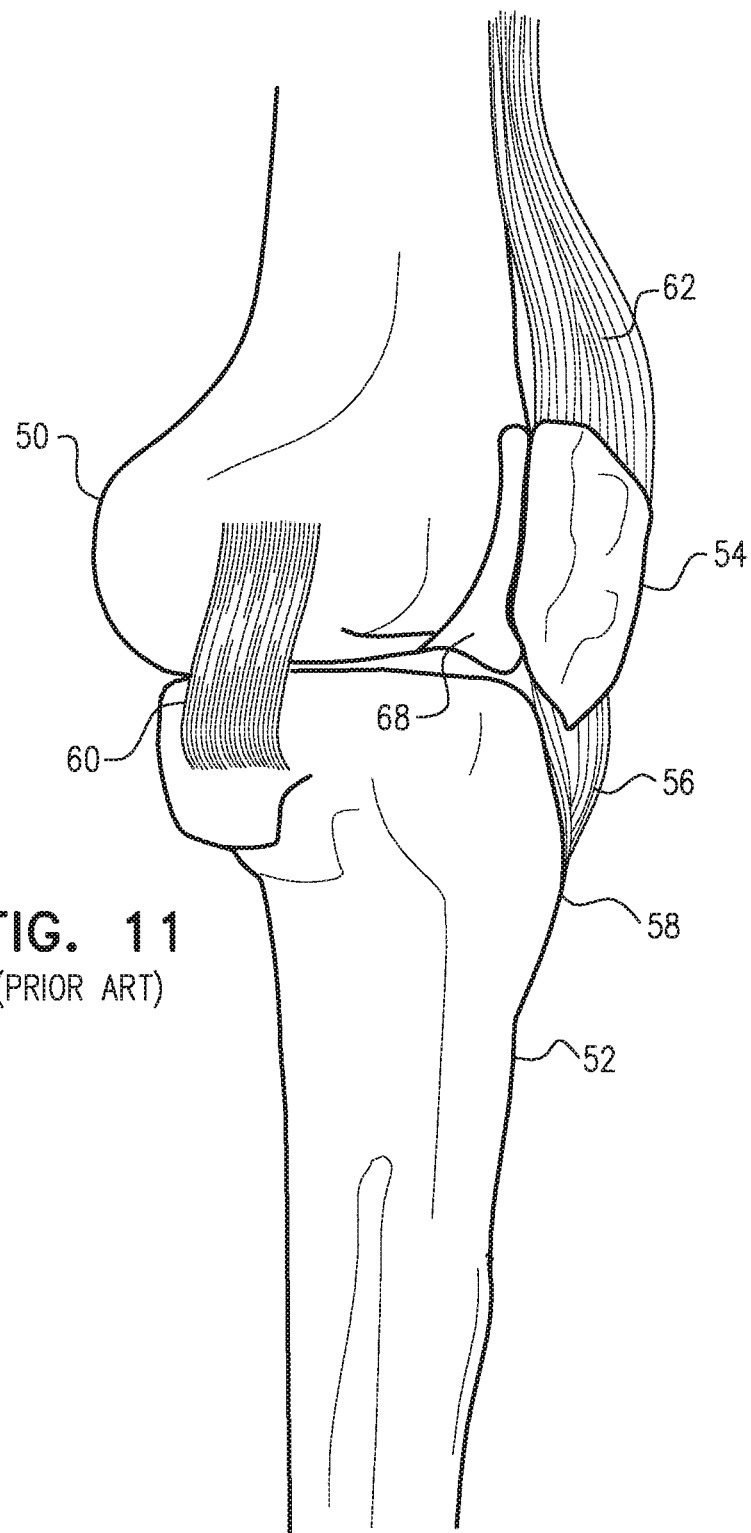
FIG. 11 is a schematic illustration of a portion of human anatomy.

Reference is now made to FIG. 11, which is a schematic illustration of a portion of human anatomy. FIG. 11 shows the tibia 52, which includes the tibial tuberosity 58, which is a large oblong elevation on the proximal, anterior aspect of tibia 52. The tibia is joined to the femur 50 via, inter alia, the lateral collateral ligament 60. The patellar tendon 56 joins tibial tuberosity 58 to the patella 54, which, in turn, is joined to femur 50 via the quadriceps tendon 62. In some pathologies, the patella is too close to the trochlea 68 of the femur (i.e., the anterior distal portion of the femur), and/or is improperly aligned with respect to trochlea 68. Applications of the present invention address this pathology, as will now be described.

Figure 12:
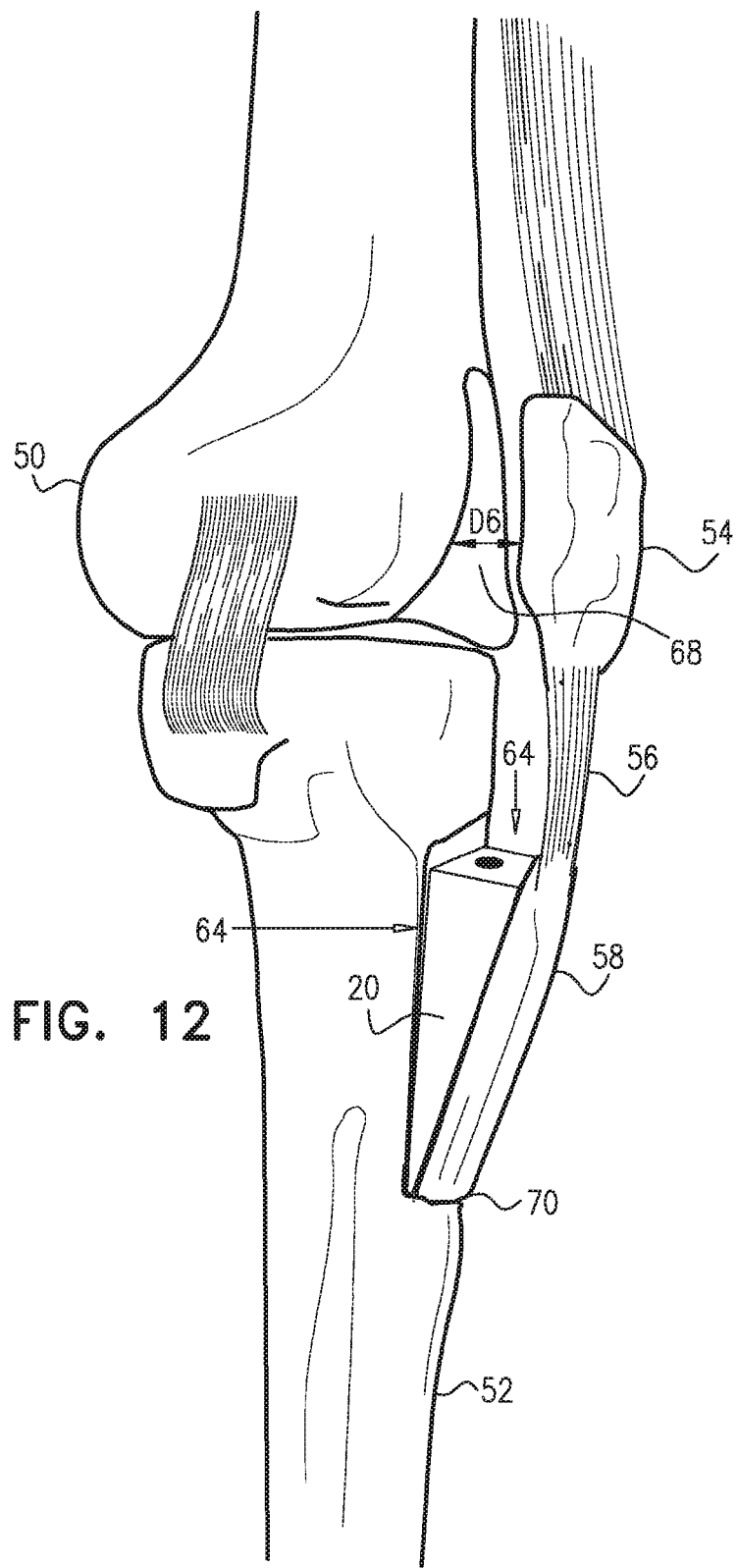
FIGS. 12-13 are schematic illustrations of an implant implanted in an osteotomy in a tibia of a subject, in accordance with some applications of the present invention.
Figure 13:
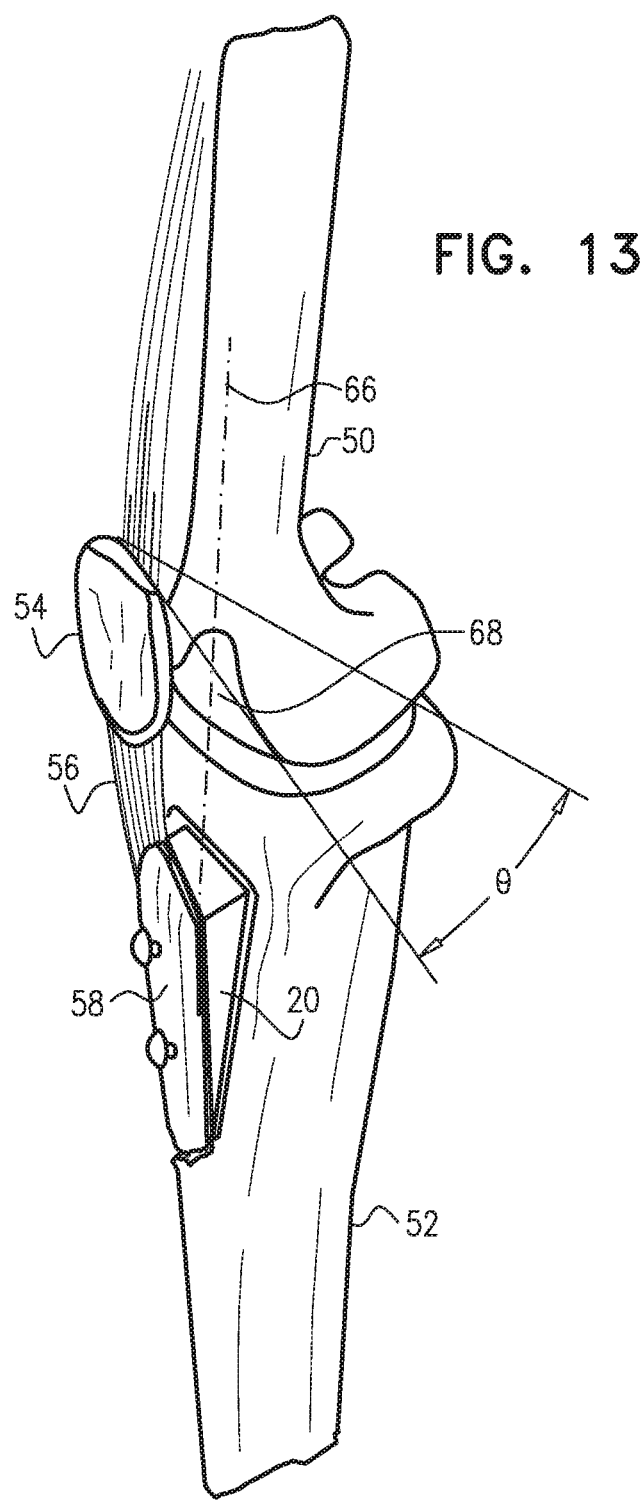

Reference is now made to FIGS. 12-13 which are schematic illustrations of implant 20 implanted in an osteotomy 64 in a tibia 52 of a subject, in accordance with some applications of the present invention.

Typically, prior to insertion of the implant, osteotomy 64 (FIG. 12) is created in the tibia. As shown in FIG. 13, the implant is then provided, and is inserted, along an axis of insertion 66, into the osteotomy. By inserting the implant in the osteotomy, tibial tuberosity 58 is rotated about axis of insertion 66, which results in a change in the angular orientation of the tibial tuberosity with respect to the other portion of the tibia. (As noted above, this rotation is facilitated by the distance between the top and bottom of the implant being greater at one side than at the other side.) Patellar tendon 56 transfers this rotational effect to patella 54, such that the patella is also rotated about axis of insertion 66, by an angle theta. Thus, the angular orientation of patella 54 is changed with respect to femur 50, and in particular, with respect to the trochlea 68 of the femur. As shown in FIG. 12, the insertion of the implant typically also increases a distance D6 of the patella from the trochlea, by pivoting the tibial tuberosity with respect to a point of contact 70 between the tibial tuberosity and the other portion of the tibia. (The pivoting of the tibial tuberosity increases a distance of the proximal portion of the tibial tuberosity from the other portion of the tibia, thus, via the patellar tendon, causing an increase in distance D6.)

As noted above, bone graft material, which is typically coupled to the implant, is typically inserted into the osteotomy, in order to help maintain the tibial tuberosity in its new position.

Reference is now made to FIGS. 14-16B, which are schematic illustrations of methods for operating on a subject, in accordance with some applications of the present invention. In some applications, by providing implant 20 and inserting it into an anatomical site, an angular orientation of a first portion of bone with respect to a second portion of bone is changed in two perpendicular planes. In other words, by inserting the implant, the first portion of bone is made to rotate about (a) axis of insertion 66, and (b) an axis 86 that is perpendicular to the axis of insertion. The anatomical site is typically surrounded at least in part by one or more bones. Typically, bone graft material, e.g., bone graft material that is coupled to the implant, is inserted into the anatomical site.

Figure 14:
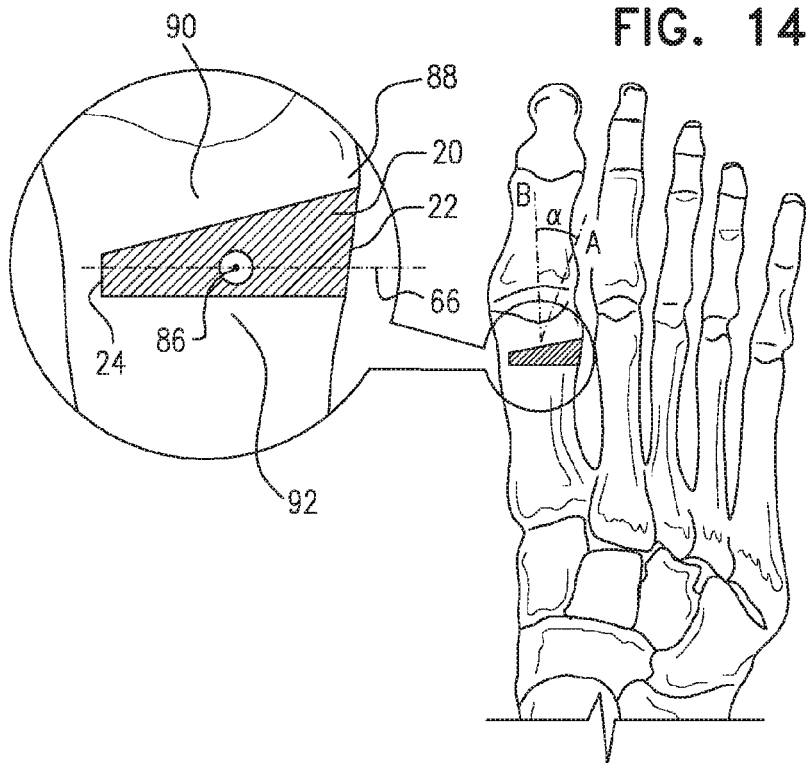
FIGS. 14, 15A, 15B, 16A and 16B are schematic illustrations of methods for operating on a subject, in accordance with some applications of the present invention.

In FIG. 14, the anatomical site is a space within a metatarsal bone 88 of the subject. Typically, an osteotomy is created in metatarsal bone 88 prior to inserting the implant, and the implant is implanted in the osteotomy. FIG. 14 shows an application in which the implant is inserted from a lateral direction, such that axis of insertion 66 runs laterally along the page, and axis 86 runs into the page. The greater height at front end 22, relative to rear end 24, facilitates a rotation, by an angle alpha, of a first portion 90 of the metatarsal bone about axis 86. Furthermore, the greater height at one of the sides, relative to the other one of the sides, facilitates a rotation by an angle theta of first portion 90 about axis 66. (This latter rotation is not shown in FIG. 14; however, it is analogous to what is shown in FIG. 13.) Thus, the angular orientation of first portion 90 is changed, in two perpendicular planes, with respect to a second portion 92 of bone 88. (Furthermore, a distance of first portion 90 from second portion 92 is increased.) The method depicted in FIG. 14 may be used, for example, to treat metatarsus adductus.

Figure 15A:
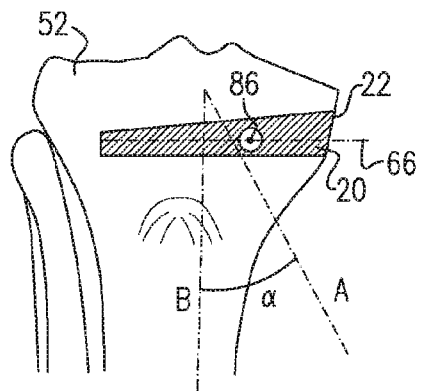
Figure 15B:
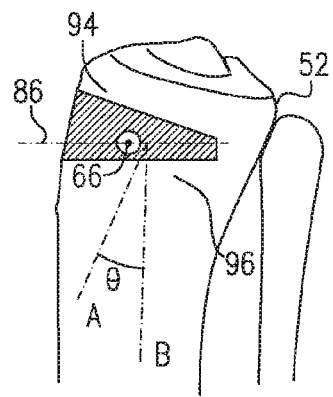

In FIGS. 15A-B, the anatomical site is a space within a tibia 52. FIG. 15A shows a frontal view of the tibia, while FIG. 15B shows a lateral view. Typically, an osteotomy is created in the tibia prior to inserting the implant. FIGS. 15A-B show an application in which the implant is inserted from a lateral direction, such that axis of insertion 66 runs laterally along the page in FIG. 15A, and into the page in FIG. 15B. The front-rear and side-side differences in height facilitate changing the angular orientation of a first portion 94 of the tibia with respect to a second portion 96 of the tibia that is more distal than first portion 94, by rotating first portion 94 about axes 66 and 86. The method depicted in FIGS. 15A-B may be used, for example, to treat varus or valgus knee.

Although FIGS. 14 and 15A-B depict a lateral insertion of the implant, it is noted that the scope of the present invention includes an insertion of the implant from other directions. (In such applications, axes 66 and 86 may be interchanged.)

Figure 16A:
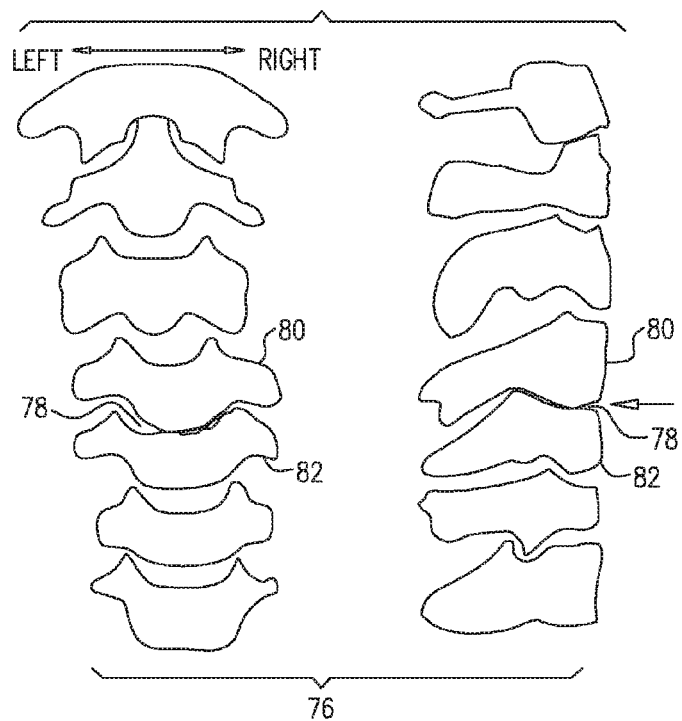
Figure 16B:
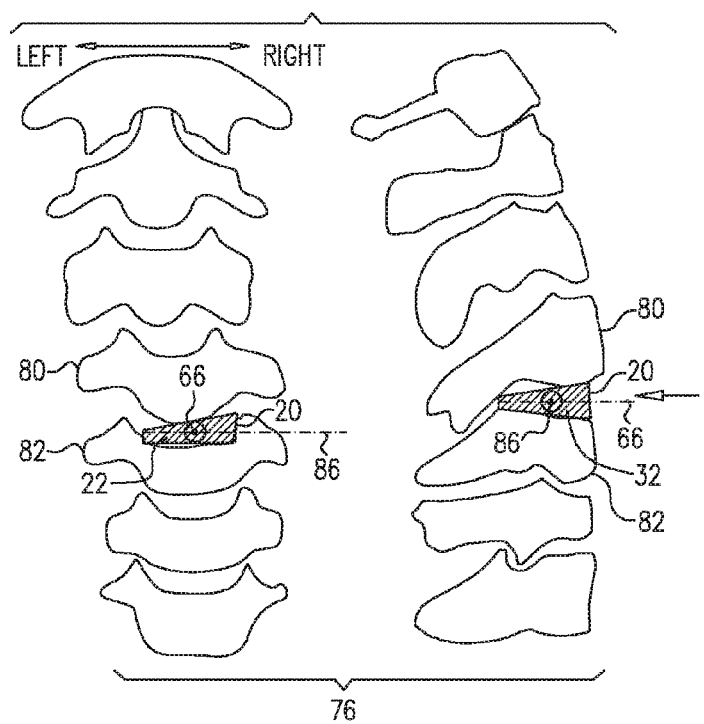

In FIGS. 16A-B, the anatomical site is a space between a first vertebra 80 and a second vertebra 82, in a cervical spine 76 of a subject. (The depicted method may also be performed on other portions of the spine.) FIG. 16A shows a frontal view (left) and lateral view (right) of spine 76 before implanting implant 20. Two pathological conditions may be observed: (i) an intervertebral space 78 between a first vertebra 80 and a second vertebra 82 of the subject is abnormally narrow, and is narrower at the right side of the spine than at the left side, and (ii) the spine is abnormally straight, i.e., normal lordosis (curvature of the spine) is lacking.

FIG. 16B shows the same two views of the spine following the implantation of the implant in intervertebral space 78. FIG. 16B shows an application in which the implant is inserted from the front or back of the spine, such that axis of insertion 66 runs into the page on the left, and laterally along the page on the right. The differences in height between the front and the rear of the implant, and between the two sides of the implant, facilitate changing the angular orientation of first vertebra 80 with respect to second vertebra 82, in addition to increasing the distance between the vertebrae. In particular, (i) due to the greater height of the implant at the right side of the implant, relative to the left side, the distance between the vertebrae is increased more at the right side than at the left side, thus restoring normal symmetry to the spinal column, and (ii) the greater height of the implant at the front of the implant, relative to the rear of the implant, facilitates the restoration of normal lordosis of the spine.

In some spinal applications, the subject lies on his back during the implantation. In such applications, the implant may be "wedged," in an anterior-to-posterior direction, into the intervertebral space. In other spinal applications, the subject lies on his front; in such applications, it is typically difficult to wedge the implant into the intervertebral space. Hence, in such applications, the intervertebral space is typically enlarged (by pulling the vertebra away from one another) before inserting the implant, in order to facilitate the insertion. Similarly, for applications in which the implant is not wedge-shaped (e.g., the height of the implant is constant), the intervertebral space may be enlarged prior to insertion of the implant.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for placement at an anatomical site, the apparatus comprising:
   an orthopedic implant, comprising:
   a front end,
   a rear end,
   a top,
   a bottom,
   a right side,
   a left side, and
   a central part connecting the right and left sides,
   wherein the implant is shaped to define an H-shape, when viewed in a direction from the top to the bottom, the right and left sides defining the legs of the H-shape and the central part of the implant defining the cross member of the H-shape;
   the implant having a top surface defining a first sloping surface running downwardly from the front end to the rear end of the implant, and the implant having a second sloping surface running downwardly from one side to the opposite side of the implant, and wherein the first and second sloping surfaces are perpendicular to each other;
   at least a portion of the implant being shaped to define a porous matrix, the porous matrix being shaped to define a plurality of pores that extend through the porous matrix in at least each of: (a) a front-to-rear direction, (b) a left-to-right direction, and (c) a top-to-bottom direction; and
   wherein at least the central part has a plurality of said pores therein, and the central part defines at least one fixation passageway that passes through the implant from the top of the implant to the bottom of the implant, the at least one fixation passageway having a diameter larger than an average diameter of the pores and is extending almost perpendicular to said second sloping surface running downwardly from one side to the opposite side of the implant.

2. The apparatus according to claim 1, wherein at least one of the right and left sides of the implant is shaped to define at least one further passageway that passes through the side, the at least one further passageway passing through the side having a diameter larger than an average diameter of the pores.

3. The apparatus according to claim 1, wherein at least 90 percent of a volume of the portion of the implant that includes the pores comprises the porous matrix.

4. The apparatus according to claim 1, wherein at least a portion of the front end, the rear end, the top, the bottom, the right side, or the left side of the implant defines a portion of the porous matrix.

5. The apparatus according to claim 1, wherein the implant is for use with a tool and the implant further comprises a connection interface that facilitates a connection of the implant to the tool.

6. The apparatus according to claim 5, wherein the connection interface is front-facing.

7. The apparatus according to claim 5, wherein the connection interface is shaped to define a threaded hole.

8. The apparatus according to claim 5, wherein the tool comprises a rod that is fixed to the implant at the connection interface.

9. The apparatus according to claim 8, wherein a connection between the rod and the implant is configured to be breakable at the connection interface due to a size of the connection interface.

10. The apparatus according to claim 1, wherein the distance between the top and the bottom is at least 0.5 mm greater at the first location at one of the sides than at the second location opposite the first location at the other one of the sides, and
    wherein the distance between the top and the bottom is at least 0.5 mm greater at the third location at the front end than at the fourth location opposite the third location at the rear end.

11. The apparatus according to claim 1, wherein the distance between the top and the bottom is greater at the front end than at respective, corresponding opposite locations on the rear end, on both of the left and the right sides of the implant.

12. The apparatus according to claim 11, wherein the distance between the top and the bottom is at least 0.5 mm greater at the front end than at the respective, corresponding opposite locations on the rear end, on both of the left and the right sides of the implant.

13. The apparatus according to claim 1, further comprising a bone graft material.

14. The apparatus according to claim 1, wherein the implant is made of a metal.

15. The apparatus according to claim 1, wherein the implant is made of a plastic.

16. The apparatus according to claim 1, wherein the implant is made of bone graft material.

17. The apparatus according to claim 1, wherein the central part defines a porous matrix.

* * * * *